United States Patent [19]
Deguchi

[11] Patent Number: 6,136,886
[45] Date of Patent: Oct. 24, 2000

[54] DENTAL ELASTIC RESTORATIVE MATERIAL AND METHOD FOR PRODUCTION OF DENTAL PROSTHETIC MATERIAL USING THE SAME

[75] Inventor: Mikito Deguchi, Kyoto, Japan

[73] Assignee: Kabushiki Kaisha Shofu, Kyoto, Japan

[21] Appl. No.: 08/985,725

[22] Filed: Dec. 4, 1997

[30] Foreign Application Priority Data

Dec. 6, 1996 [JP] Japan ................... 8-326579

[51] Int. Cl.$^7$ ................... A61K 6/083
[52] U.S. Cl. ................... 523/116; 523/113; 523/115; 524/264; 524/533; 524/535; 526/301
[58] Field of Search ................... 523/113, 115, 523/116; 524/533, 535, 264; 526/301

[56] References Cited

U.S. PATENT DOCUMENTS

| | | | |
|---|---|---|---|
| 3,929,693 | 12/1975 | Hochberg | 260/885 |
| 4,225,696 | 9/1980 | Colpitts et al. | 528/76 |
| 4,308,190 | 12/1981 | Waskowiak et al. | 523/116 |
| 4,347,174 | 8/1982 | Nagase et al. | 526/301 |
| 4,396,476 | 8/1983 | Roemer et al. | 523/115 |
| 4,782,100 | 11/1988 | Iwamoto et al. | 523/113 |
| 5,210,109 | 5/1993 | Toteosian et al. | 523/109 |
| 5,591,786 | 1/1997 | Oxman et al. | 523/109 |

FOREIGN PATENT DOCUMENTS

| | | |
|---|---|---|
| 0514096 | 11/1992 | European Pat. Off. |
| 1374670 | 11/1974 | United Kingdom |
| 2173506A | 10/1986 | United Kingdom |
| 9116013 | 10/1991 | WIPO |

*Primary Examiner*—Andrew E. C. Merriam
*Attorney, Agent, or Firm*—Stevens, Davis, Miller & Mosher, L.L.P.

[57] ABSTRACT

To provide a dental prosthetic material having processing characteristics and operating characteristics, which are not recognized in a conventional dental material.

A biorestorative material which is a rubber elastic material having a shear modulus of 1.0–9.99 E+4 Pa to 1.0–9.99 E+9 Pa and a rubber hardness of 1 to 90, wherein a Knoop hardness can be 10 or more after polymerization.

21 Claims, 1 Drawing Sheet

DENTAL ELASTIC RESTORATIVE MATERIAL AND METHOD FOR PRODUCTION OF DENTAL PROSTHETIC MATERIAL USING THE SAME

BACKGROUND OF THE INVENTION

1. Field of the Invention

The present invention relates to a novel biorestorative material which is a rubber elastic material, wherein a Knoop hardness can be 10 or more after polymerization.

The biorestorative material of the present invention is a material for restoring the living body, and is specifically used as dental prosthetic materials (e.g. artificial tooth, connector tooth, veneer crown, interim prosthesis, denture base material, etc.), contact lens and nail prosthetic materials. The biorestorative material can also be used as toy materials, general industrial materials, etc.

2. Description of the Prior Art

<Artificial tooth>

An artificial tooth is used in anterior tooth, molar, connector tooth, etc., and is molded by charging a polymerizable compound in a mold under a pressure, and polymerizing under the molding conditions wherein a suitable temperature and time are selected. As the material, a mixed system of polymethyl methacrylate (hereinafter abbreviated to "PMMA") and methyl methacrylate (hereinafter abbreviated to "MMA") or a composite material composed of a high-viscosity polyfunctional methacrylate represented by 7,7,9-trimethyl-4,13-dioxo-3,14-dioxo-5,12-diaza-hexadecane-1,16-diol-dimethacrylate (hereinafter abbreviated to "UDMA") and an inorganic/organic filler has hitherto been used. The artificial tooth is polymerized in the mold, and designed so that the Knoop hardness is from about 11 to 50. It occupies an important position in the dental treatment to repair a missing tooth due to coming out of a natural tooth, and abrasion, coming out, breakage, etc. of a ready-made artificial tooth after production of a denture according to a normal dental method. In general, it is a normal method to conduct morphological correction extraorally using a ready-made resin tooth. Taking the burden and adaptability of patients into consideration, a more precise one can be produced in a shorter time when the morphological correction is conducted in the state where the denture is mounted. However, since a ready-made tooth is hard, it is difficult to deform the ready-made tooth by applying a physical force intraorally or on a model.

<Dental crown restorative material>

There are resin jacket crown, resin veneer crown, etc. having the color tone of a dental crown used when the aesthetic property of the missing dental crown is recovered with a restored piece. As the material, a rigid resin as a mixture of a polyfunctional monomer and an inorganic filler is generally used. On the other hand, an interim prosthesis is a restored piece used temporarily for the purpose of supplying maintenance of occlusion, improvement, pronunciation, masticatory efficiency, etc. for a fixed period until a final prosthetic treatment is conducted. For example, for the purpose of performing protection of the tooth quality or marginal gingiva of the abutment tooth, prevention of secondary caries, prevention of migration of adjacent teeth, recovery of the aesthetic property, etc., a ready-made shell crown, a shell molar and a temporary cover crown produced by using an acrylic cold-polymerizable resin are exclusively used.

<Method for production of artificial tooth>

An integrated artificial tooth is obtained by charging those, prepared by coloring a mixed system of MKA and PMMA, or a composite material in an enamel color, an dentin color or a base color, in a mold, heating under pressure, and performing stepwise molding with changing the mold in order, for example, the enamel portion, dentin portion and then base portion in FIG. 1 and FIG. 4, and the enamel portion and then base portion in FIG. 2 and FIG. 3. As a matter of course, the order of the mold may be reversed. Basically, the artificial tooth is molded under the molding condition that the initial molding is not completed in case of molding each portion, and all molding portions are completely polymerized at the time of the final molding and, furthermore, the chemical reaction between the enamel portion and dentin portion and that between the dentin portion and base portion are performed to bond each other. Since the molded artificial tooth is produced by multi-layer molding, it has burr of the polymerized material. Therefore, a final artificial tooth is completed by passing through a so-called polishing step after crude finishing using a tumbler or hand correction.

Since a conventional artificial tooth and connector tooth are completely polymerized, they are not deformed by a suitable pressure on a wax model denture or a denture base and, therefore, occlusal adjustment can not be performed. In addition, the connector tooth can not be deformed according to steepness of a dental arch and, therefore, considerable time and technique were required to the repair of the denture or production of the denture base.

Since a conventional shell and shell molar are completely polymerized, they are not deformed by a suitable pressure. Therefore, it was difficult to adapt them to the shape of the abutment tooth.

It is difficult to perform morphological correction of a conventional dental crown restorative material for repairing the dental crown surface of the denture or the surface of the natural tooth. Furthermore, it is difficult to reproduce a color tone in a simple and stable manner because a suitable forming and coloring are not provided. Therefore, the quality of repair of the dental crown varied with each dental technician. In addition, it was impossible to bond it directly to the abutment tooth intraorally.

A large-sized thermal/pressure molding machine is required to a conventional method for production of an artificial tooth, and conditions wherein bonding is taken into consideration are required as the molding conditions. Therefore, the range of the molding conditions is narrow and was not easily set.

SUMMARY OF THE INVENTION

One of the purpose of the present invention is to provide a biorestrative materials a rubber elastic material having a Knoop hardness after polymerization of 10 or more;

Another purpose of the present invention is to provide a curable dental prosthetic material comprising said biorestrative material; and Further, purpose of the present invention is to provide a dental prosthetic material obtained by said curable dental prosthetic material.

The biorestrative material according to the present invention comprises polymers, polymerizable monomers, a silane-treated silica-dispersed uniformly in urethane (meth) acrylate and a polymerization initiator.

DETAILED DESCRIPTION OF THE INVENTION

Figure 1:
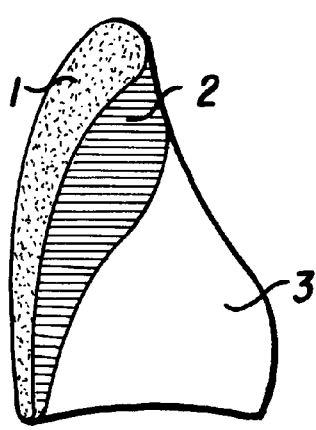
FIG. 1 is a structural schematic diagram of a anterior tooth comprising an enamel portion, a dentinal portion and a base portion.
Figure 2:
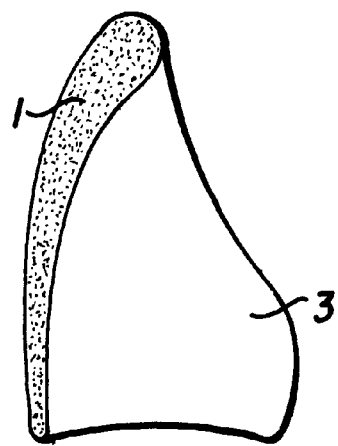
FIG. 2 is a structural schematic diagram of an anterior tooth comprising an enamel portion and a base portion.
Figure 3:
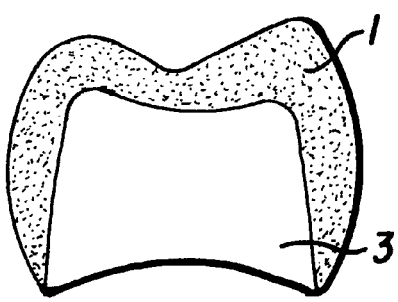
FIG. 3 is a structural schematic diagram of a molar comprising an enamel portion, a dentinal portion.
Figure 4:
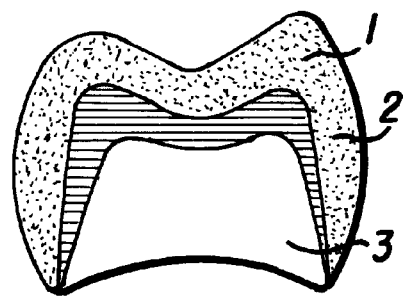
FIG. 4 is a structural schematic diagram of a molar comprising an enamel portion, a dentinal portion and a base portion.

The present invention relates to a biorestorative material like rubber elastic materials and having characteristics capable of maintaining a shear modulus of $1.0 \times 10^4$ Pa to $9.99 \times 10^9$ Pa and a rubber hardness of 1 to 90 until polymerization, wherein a Knoop hardness can be 10 or more after polymerization.

More preferably, the present invention relates to the above biorestorative material comprising 14.5 to 62.5% by weight of a polymer, 10.0 to 37.5% by weight of d polymerizable monomer, 10.0 to 60.0% by weight of a silane-treated silica-dispersed uniformly in urethane (meth)acrylate and a polymerization initiator.

The present invention also relates to a dental prosthetic material obtained by using the above biorestorative material.

The biorestorative material of the present invention can be used as a novel dental prosthetic material, and it is possible to make the best use of the applicability and characteristics, which are not recognized in conventional artificial tooth and dental crown restorative material.

The biorestorative material of the present invention is not deformed when removing artificial tooth and dental crown restorative material from the mold. Furthermore, the biorestorative material can maintain the shear modulus or rubber hardness for a long period of time and can be deformed by applying a suitable pressure. It is possible to perform morphological correction of the biorestorative material, easily.

Furthermore, when the biorestorative material of the present invention is used as the artificial tooth or movable connector tooth, the occlusal adjustment can be easily performed on the wax model denture or denture base by making use of the shear modulus and rubber hardness. With respect to the movable connector tooth, it becomes possible to adapt to the steepness of the dental arch, thereby making it possible to produce a denture, simply and precisely.

In general, the dental crown restorative material is liable to be influenced by an ability of the dental technician. According to the biorestorative material of the present invention, it is possible to perform the morphological correction before polymerization. A suitable forming and coloring are previously provided, and it is possible to easily produce a dental crown restorative material having stable quality regardless of the ability of the producer. As a matter of course, correction can be performed according to the same manner as that used in a conventional dental crown restorative material even after polymerization, if necessary. The biorestorative material of the present invention can be used intraorally/extraorally.

Furthermore, the present invention has the following feature. That is, a stepwise heat molding considering the bonding is not required so as to perform polymerization after removing from the mold, and it is possible to produce an artificial tooth which has little burr and is superior in moldability, bonding characteristics and aesthetic property.

The biorestorative material of the present invention has a feature of maintaining a shear modulus of at least $1.0 \times 10^4$ Pa to $9.99 \times 10^9$ Pa and a rubber hardness of at least 1 to 90 until the polymerization is conducted. The maintenance of the shear modulus or rubber hardness means that, after storage at the temperature of 4 to 35° C., the shear modulus and rubber hardness measured at the temperature within the range from 20 to 25° C. are maintained for at least 3 months. More preferably, the shear modulus and rubber hardness are maintained for 2 years.

Regarding the biorestorative material of the present invention, an aged mixture prepared by mixing in specific components or a specific mixing ratio can be formed into the artificial tooth and dental crown restorative material, using a mold, thereby affording a biorestorative material capable of performing the morphological correction.

The biorestorative material of the present invention will be described in detail hereinafter.

The term "uniform dispersion" used in the present invention means that the transmittance of the silane-treated silica-dispersed uniformly in urethane (meth)acrylate before and after curing is not less than 80%. The transmittance at 750 nm to 380 nm was measured by using a spectrophotometer U-3200 (manufactured by Hitachi, Ltd.).

The polymer used in the present invention is a polymer or copolymer of polyalkyl (meth)acrylate of PMMA or polymethyl methacrylate (hereinafter abbreviated to "PEMA"), or a homopolymer or copolymer of a polymer wherein a nucleus of polymer particles is composed of crosslinked polyalkyl (meth)acrylate and a shell is composed of PMMA or PEMA, etc. It is necessary that the above polymer is swollen with or dissolved in a polymerizable monomer at room temperature in a short period of time. The polymer, wherein the nucleus is composed of a crosslinked polymer and is not swollen with or dissolved in the polymerizable monomer and the shell is made of PMMA, is more effective when an elastomer is prepared. From such a point of view, it is suitable to use those having an average molecular weight of 100,000 to 1,000,000, preferably 200,000 to 1,000,000, and an average particle diameter of 1 to 100 μm, preferably of 1 to 75 μm as the polymer. As used throughout the specification and claims, the term "average molecular weight" means "weight average molecular weight."

Specific examples of the polymerizable monomer of the present invention include monofunctional monomers having one ethylenically unsaturated bond, such as MMA, ethyl (meth)acrylate, butyl (meth)acrylate, 2-hydroxyethyl methacrylate (hereinafter abbreviated to "2-HEMA"), etc.; polyfunctional monomers having two or more ethylenically unsaturated bonds, such as ethylene glycol di(meth)acrylate (hereinafter abbreviated to "EG"), triethylene glycol di(meth)acrylate (hereinafter abbreviated to "TG"), trimethylolpropane trimethacrylate (hereinafter abbreviated to "TMPT"), etc.; and reaction composition of phosphonyl chloride and 2-hydroxyethyl methacrylate (hereinafter abbreviated to "PPZ"), such as 2,2-bis[4-methacryloxyphenyl]propane di(meth)acrylate (hereinafter abbreviated to "D-2.6E"), and urethane (meth)acrylate such as UDMA, etc. Among them, MMA, 2-HERA, EG, TG, TMPT, D-2.6E and UDMA are preferable. MMA, EG, TG and TMPT are more preferable.

The urethane (meth)acrylate of the present invention has at least one acryloyl group and/or methacryloyl group as well as at least one urethane group in one molecule, and typical examples thereof include UDMA, 1,6-bis[(2-phenoxy-2'-acryloxy)isopropyl-oxy-carbonylamino]hexane (hereinafter abbreviated to "UDA") and 1,1,1-tri[6[(1-acryloxy-3-phenoxy)isopropyloxycarbonylamino]- hexylcarbamoyloxymethyl]propane (hereinafter abbreviated to "URO"). The urethane (meth)acrylates represented by the following formula:

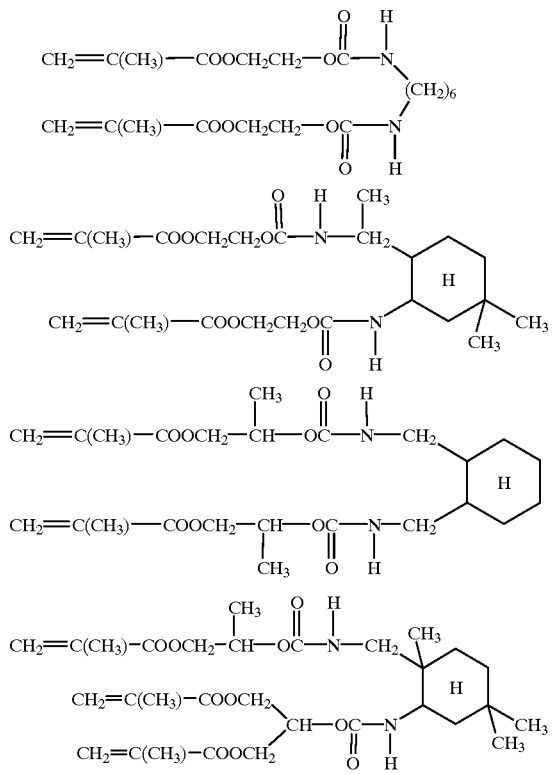

are also preferable. Basically, those wherein a principal chain backbone of the urethane bond may be an aliphatic, aromatic or alicyclic group, and those which contain neither aromatic nor alicyclic groups in the principal chain backbone, but contain aliphatic, aromatic and alicyclic groups in the side chain are more preferable. Particularly preferable urethane (meth)acrylates are UDMA, UDA and URO.

The silica-dispersed urethane (meth)acrylate in the present invention is a composition wherein colloidal silica having an average particle diameter (primary particles) of 1 to 85 nm are uniformly dispersed in urethane (meth)acrylate. Preferably, the content of the urethane (meth)acrylate is from 29.0 to 69.0% by weight, the content of the colloidal silica is from 10.0 to 70.0% by weight, and the content of the silane compound is from 1.0 to 30.0% by weight. The colloidal silica is treated with a silane compound represented by the formula (I);

$$Y_nSiX_{4-n} \quad (I)$$

wherein Y represents a hydrocarbon group or a vinyl-polymerizable reactive group; X represents a hydrolyzable group; and n represents a numerical value of 1, 2 or 3.

As the solvent-dispersed colloidal silica used in the present invention, various commercially available products can be used. The preferable particle diameter of the colloidal silica is from 1 to 85 nm. As the colloidal silica, various commercially available products can be used and examples thereof include those which are sold under the trade name of Snowtex IPA-ST (manufactured by Nissan Chemical Industries, Ltd.)(hereinafter abbreviated to "IPA-ST") (average particle diameter: 10 to 15 nm), OSCAL-1432 (manufactured by Shokubai Kasei Kogyo Co., Ltd.) (average particle diameter: 10 to 20 nm) and OSCAL-1632 (manufactured by Shokubai Kasei Kogyo Co., Ltd.) (average particle diameter: 11 nm)(the term "average particle diameter" used herein means an average particle diameter of primary particles). The dispersion medium of the colloidal silica is not specifically limited, but water, methanol, alcohols (e.g. isopropyl alcohol, etc.), cellosolves and dimethylacetamides may be used. Particularly preferable dispersion mediums are alcohols, cellosolves and water.

The silane compound used in the present invention is that represented by the general formula (I):

$$Y_nSiX_{4-n} \quad (I)$$

wherein Y represents a hydrocarbon group or a vinyl-polymerizable reactive group; X represents a hydrolyzable group; and n represents numerical value of 1, 2 or 3. The hydrocarbon group represents a hydrocarbon group such as an alkyl group, preferably, having 1 to 3 carbon atoms, a phenyl group, etc. or a mixture thereof. The vinyl-polymerizable reactive group represents a vinyl group, an acrylic group or a methacrylic group, or a mixture thereof. The hydrolyzable group has a property of eliminating in an acid catalyst, and specific examples thereof include alkoxy group, methoxyalkoxy group, acetoxy group and phenyloxy group.

Examples of the silane compound represented by the general formula (I) include methyltriethoxysilane, ethyltrimethoxysilane, phenyltrimethoxysilane, phenyltriethoxysilane, methylphenyldiethoxysilane, trimethylmethoxysilane, trimethylethoxysilane, methoxyethyltriethoxysilane, acetoxyethyltriethoxysilane, methyltriacetoxysilane, methyltris(acryloxyethoxy) silane, methyltris(methacryloxyethoxy) silane, β-methacryloxyethyldimethoxymethylsilane, γ-acryloxypropylmethoxydimethylsilane, β-methacryloxyethyldimethoxymethylsilane, γ-methacryloxypropylmethoxydimethylsilane, γ-methacryloxypropyldimethoxysilane, γ-methacryloxypropyltrimethoxysilane, vinylmethyldimethoxysilane, vinyltrimethoxysilane, vinyltriethoxysilane, p-vinylphenyldimethoxysilane and the like.

| | |
|---|---|
| $CH_3Si(OC_2H_5)_3$ | (I-1) |
| $C_6H_5Si(OCH_3)_3$ | (I-2) |
| $CH_2=CHSi(OC_2H_4H_3)_3$ | (I-3) |
| $CH_2=CHSi(OCH_3)_3$ | (I-4) |
| $CH_2=CHSi(OC_2H_5)_3$ | (I-5) |
| $CH_2=CCH_3COOC_3H_6Si(OCH_3)_3$ | (I-6) |

The silane compounds represented by the above structural formulas are methyltriethoxysilane (I-1), phenyltrimethoxysilane (I-2), vinyltris(β-methoxyethoxy) silane (I-3), vinyltrimethoxysilane (I-4), vinyltriethoxysilane (I-5) and γ-methacryloxypropyltrimethoxysilane (I-6).

These silane compounds may be used alone or in combination thereof. Also, there may be used a silane compound wherein Y may has an alkyl group and a vinyl-polymerizable reactive group in one molecule, or used a silane compound wherein Y is an alkyl group in combination with a silane compound wherein Y is a vinyl-polymerizable reactive group. It is preferable to use the silane compound wherein Y is an alkyl group in combination with the silane compound wherein Y is a vinyl-polymerizable reactive group. More preferable one is a silane compound wherein Y is a vinyl-polymerizable reactive group.

According to the silane treatment of the colloidal silica, the silane compound is hydrolyzed by using an acid catalyst. In the hydrolysis reaction, a solvent can be used to perform an uniform reaction. The solvent is preferably a solvent capable of compatibilizing silane alkoxide as the reaction product with water and a catalyst. Examples of the solvent include water, methyl alcohol, ethyl alcohol, n-propyl alcohol, isopropyl alcohol, n-butyl alcohol, t-butyl alcohol, pentanol, ethylene glycol, diethylene glycol, glycerin, ethylcellosolve and the like. Among them, methyl alcohol, ethyl alcohol, n-propyl alcohol and isopropyl alcohol are particularly preferable. The silane compound in the state of being mixed with colloidal silica in the solvent is hydrolyzed at the temperature of room temperature to about 120° C., preferably about a boiling point of the solvent, for 30 minutes to 24 hours, preferably about 1 to 10 hours.

The amount of the silane compound represented by the structural formula (I-1 or I-2) is preferably from 2 to 35% by weight based on 65.0 to 98% by weight of the colloidal silica solid content, more preferably from 2 to 30% by weight based on 70.0 to 98% by weight of the colloidal silica solid content.

The amount of the silane compound represented by the structural formula (I-3, I-4, I-5 or I-6) is preferably from 2.0 to 35.0% by weight based on 65.0 to 98.0% by weight of the colloidal silica solid content, more preferably from 2.0 to 30.0% by weight based on 70.0 to 98.0% by weight of the colloidal silica solid content.

When using at least one compound represented by the structural formula (I-1 or I-2) in combination with at least one compound represented by the structural formula (I-3, I-4, I-5 or I-6), the amount of the silane compound represented by the structural formula (I-1 or I-2) is preferably from 1.0 to 34.0% by weight based on 65.0 to 98.0% by weight of the colloidal silica solid content, and the amount of the silane compound represented by the structural formula (I-3, I-4, I-5 or I-6) is preferably from 1.0 to 34.0% by weight.

As the method of dispersing the solvent-dispersed colloidal silica in urethane (meth)acrylate, a method of mixing a silane compound and, if necessary, water and a catalyst with a dispersion of colloidal silica, reacting the mixture under the above-described reaction conditions, mixing this reaction solution with urethane (meth)acrylate and then removing a dispersion medium of the solvent dispersion colloidal silica and a hydrolysis reaction product of the silane compound is particularly preferable. The silane-treated silica-dispersed uniformly in urethane (meth)acrylate in the present invention can be prepared as follows.

In order to uniformly disperse the silane-treated silica in the solvent-dispersed colloidal silica, a reaction device equipped with a separable flask, a three inlet cover, AuUbc, a mercury seal, a stirring bar, a stirring leaf, a separatory funnel, a condenser and a catch (manufactured by Kiriyama Seisakusho Co.) is preferably used. Then, the dispersion medium of colloidal silica in the dispersion and hydrolysis reaction product of the silane compound are removed. The dispersion medium, solvent and other comparatively volatile substances are preferably removed under reduced pressure. More preferably, the volatile solvent is removed with adding dropwise urethane (meth)acrylate to the reaction system through a separatory funnel. Thus, the uniformly dispersed dental curable composition of the present invention can be prepared.

The expression "a homogeneous composition containing a poly(alkyl methacrylate) and an urethane (meth)acrylate showing neither solubility nor swelling properties to said poly(alkyl methacrylate) shows the solubility or swelling properties" means that the poly(alkyl methacrylate) is homogeneously swollen with or dissolved in the urethane (meth) acrylate showing inherently neither solubility nor swelling properties to the poly(alkyl methacrylate), thereby forming a high-viscosity transparent mixed solution. In the mixed solution, no poly(alkyl methacrylate) particles are visually observed and, in principle, the poly(alkyl methacrylate) is not sedimented with a lapse of days.

In the present invention, the homogeneous composition containing a poly(alkyl methacrylate) and an urethane (meth)acrylate showing neither solubility nor swelling properties to the poly(alkyl methacrylate) can be obtained by reacting an isocyanate compound with (meth)acrylate in a homogeneous phase solution of a poly(alkyl methacrylate) and a hydroxyl group-containing (meth)acrylate compound, or reacting a hydroxyl group-containing (meth)acrylate with isocyanate in a homogeneous phase solution of a polymer and an isocyanate compound, in the reverse order.

In the resulting composition, the urethane (meth)acrylate is homogeneously blended at the molecular level in the poly(alkyl methacrylate). Such a composition has high transparency and the cured composition has a feature such as increase in crosslink density, refining of layer structure, increase in strength of bonding between layers, etc.

The poly(alkyl methacrylate) (which may include various type of derivertives as referred to hereinafter, but they are simply referred to "poly(alkyl methacrylate)" in the specification) used in the homogeneous composition containing a poly(alkyl methacrylate) and an urethane (meth) acrylate showing neither solubility nor swelling properties to the poly(alkyl methacrylate) is PMMA or PEMA having an average molecular weight of 100,000 to 1,000,000 and an average particle diameter of 1 to 75 $\mu$m. It is possible to apply the method of using PEMA and/or PMMA to any poly(alkyl methacrylate)s. These poly(alkyl methacrylate)s can be dissolved in or swollen with hydroxyl group-containing (meth)acrylate or any one of aliphatic isocyanate such as trimethylhexamethylene diisocyanate (hereinafter abbreviated to "TMDI"), alicyclic isocyanate and aromatic isocyanate compounds, etc. That is, the above poly(alkyl methacrylate) is homogeneously swollen or dissolved by mixing with the hydroxyl group-containing (meth)acrylate compound or isocyanate compound, thereby forming a high-viscosity transparent mixed solution.

Suitable examples of the hydroxyl group-containing (meth)acrylate used in the present invention include 2-HEMA, 3-hydroxypropyl methacrylate, 4-hydroxybutyl methacrylate, 5-hydroxypentyl methacrylate, 6-hydroxyhexyl methacrylate, 2-hydroxy-3-phenyloxypropyl methacrylate (hereinafter abbreviated to "2-HPPA"), 2-hydroxyethyl acrylate, 3-hydroxypropyl acrylate, etc., preferably 2-HEMA, 2-HPPA and 3-hydroxypropyl methacrylate, more preferably 2-HEMA and 2-HPPA.

On the other hand, suitable examples of the isocyanate compound include trimethylhexamethylene diisocyanate (hereinafter abbreviated to TMDI) hexamethylene diisocyanate (hereinafter abbreviated to "HMDI"), bisphenol A diisocyanate, dicyclohexyldimethylmethane diisocyanate, isophorone diisocyanate (hereinafter abbreviated to "IPDI"), tolylene diisocyanate, xylylene diisocyanate, diphenylmethane diisocyanate, naphthalene diisocyanate, etc., preferably TMDI, HMDI and IPDI, more preferably TMDI and HMDI.

It is also possible to use a polyisocyanate having an isocyanat group at the terminal, obtained by reacting polyol with excess diisocyanate. Examples of the polyol include ethylene glycol, diethylene glycol, triethylene glycol, tetraethylene glycol, propylene glycol, 1,4-butanediol, 2,3-butanediol, 1,1,1-trimethylolpropane, glycerin, etc. As the diisocyanate, those described above may be used without causing any problem.

In the present invention, "a homogeneous composition containing a poly(alkyl methacrylate) and an urethane (meth)acrylate showing neither solubility nor swelling properties to said poly(alkyl methacrylate)" means a composition wherein the poly(alkyl methacrylate) and urethane (meth)acrylate are uniformly blended.

Said homogeneous composition can be obtained by the following procedures. For example, a hydroxyl group-containing (meth)acrylate such as 2-HEMA, etc. is charged in a flask and, after blowing a nitrogen gas, the (meth)acrylate is heated to 40 to 50° C. With stirring at a rate of 50 to 80 rpm, a poly(alkyl methacrylate) is added by small portions and then completely swollen/dissolved.

Then, a tin catalyst used generally in synthesis of urethane is dissolved therein and, after dissolving, the atmosphere of the flask is replaced by an oxygen gas. With blowing this gas, an isocyanate compound such as TMDI, etc. is added dropwise over 2 to 3 hours. Normally, a slightly excess amount of the diisocyanate is used. After the completion of the dropwise addition, the mixture is heated to 70±1° C. to obtain a desired product.

The desired product can also be produced by charging TMDI in the flask, and adding a hydroxyl group-containing (meth)acrylate such as 2-HEMA, in the reverse order.

When using the polyisocyanate having an isocyanate at the terminal, obtained by reacting polyol with excess diisocyanate, a polyhydric alcohol (number of hydroxyl groups: 2 to 4) is reacted in a homogeneous phase solution of a polymer and isocyanate, and then the reactive terminal isocyanate group may be reacted with the hydroxyl group-containing (meth)acrylate.

The amount of the polymer added is suitably from 5.2 to 47 g based on 1 mol of the isocyanate compound such as UDMA, etc.

As the plasticizer used in the present invention, a phthalate plasticizer is preferable. Examples of the phthalate plasticizer include phthalate derivatives represented by dimethyl phthalate (hereinafter abbreviated to "DMP"), dibutyl phthalate (hereinafter abbreviated to "DBP") and dioctyl phthalate.

In case of the biorestorative material of the present invention, the following fact is important. That is, when polymerizable monomer, silane-treated silica-dispersed uniformly in urethane (meth)acrylate, polymerization initiator and/or the homogeneous composition containing a poly (alkyl methacrylate) and the urethane (meth)acrylate showing neither solubility nor swelling properties to the poly (alkyl methacrylate) and/or a plasticizer are mixed with the polymer, the monofunctional monomer in the polymerizable monomer (e.g. MMA, etc.) is swollen and diffused, and then the homogeneous composition containing a poly(alkyl methacrylate) and an urethane (meth)acrylate showing neither solubility nor swelling properties to the poly(alkyl methacrylate) or the silane-treated silica-dispersed uniformly in urethane (meth)acrylate, constitutes a matrix portion and maintains an elastomer for a long period. Therefore, the urethane (meth)acrylate must have a molecular weight higher than that of MMA, and must not show swelling properties and physical properties such as toughness and transparency after polymerizing. Therefore, it is a large feature to contain the silane-treated silica-dispersed uniformly in urethane (meth)acrylate and optionally said homogeneous composition.

The biorestorative material of the present invention maintains suitable elasticity, and can be repaired easily by using scissors or a sharp cutting knife on use. If necessary, it can be surface-treated with an organic solvent (e.g. methylene chloride, acetone, ethyl acetate, etc.) or a polymerizable monomer, and has a large feature in bonding properties.

As the method of mixing the polymer, polymerizable monomer, silane-treated silica-dispersed uniformly in urethane (meth)acrylate, polymerization initiator and/or the homogeneous composition containing a poly(alkyl methacrylate) and an urethane (meth)acrylate showing neither solubility nor swelling properties to the poly(alkyl methacrylate), and/or a plasticizer, there can be used methods such as (1) mortar mixing, (2) vessel mixing, (3) ball mill mixing, etc., but ball mill mixing and double planetary mixing are more preferable. In the present invention, the ball mill mixing was used. The ball mill mixing was performed using a laboratory planetary ball mill [P-5, manufactured by Flitchu Japan Co., Ltd.]. The mixing conditions are as follows: room temperature, 50 to 250 rpm, mixing time of 5 to 60 minutes and 4 to 10 pebbles (10 mm$\phi$).

The preferable mixing conditions in case of using the laboratory planetary ball mill P-5 are as follows: room temperature, 50 to 250 rpm, mixing time of 5 to 60 minutes and 4 to 10 pebbles (10 mm$\phi$). Heating is not required to the mixing and sufficiently uniform mixing could be conducted at room temperature (23° C.). In case of mixing, the atmosphere in the ball mill and the mixture are preferably replaced by an inert gas.

The method of producing dental prosthetic materials such as artificial tooth, movable connector artificial tooth, dental crown restorative material, etc. is as follows. That is, a mixture containing a polymer, polymerizable monomer, silane-treated silica-dispersed (uniformly) urethane (meth) acrylate and polymerization initiator and/or a homogeneous composition containing a poly(alkyl methacrylate) and the urethane (meth)acrylate showing neither solubility nor swelling properties to the polyalkyl methacrylate, and/or a plasticizer, is charged in a mold for artificial tooth, a mold for connector artificial tooth, a mold or plaster cast for dental crown material. After preliminary pressing under 20 to 500 kgf/cm$^2$ for 10 to 120 minutes, the resultant is removed from the mold and the forming is retouched. The biorestorative material is preferably stored at room temperature (35° C. or less), more preferably in a simple closed vessel at 5 to 25° C. In case of the photopolymerization type, it is necessary to conduct light screening to avoid ultraviolet light and visible light, as a matter of course.

It is possible to optionally select the polymerization initiator in the present invention according to the polymerization form suitable for the purpose. In order to polymerize the biorestorative material, the temperature is preferably within the range from 50 to 150° C. In this case, a peroxide is effective as the polymerization initiator and is added in the amount of 0.1 to 3.0 parts by weight based on 100 parts by weight of a mixture containing silane-treated silica-dispersed uniformly in urethane (meth)acrylate and/or the homogeneous composition. As the peroxide, for example, lauroyl peroxide, benzoyl peroxide (hereinafter abbreviated to "BPO") and 1,1-bis-t-butylperoxycyclohexane are preferable. In case of polymerizing with ultraviolet light and visible light, a photopolymerization initiator and a reducing agent are added in the amount of 0.2 to 3.0 parts by weight based on 100 parts by weight of a mixture containing the polymerizable monomer, colloidal silica-dispersed polymerizable monomer and the homogeneous composition. As the photopolymerization initiator, for example, a-diketone compound, ketal compound and anthraquinone compound are effective, and camphor quinone (hereinafter abbreviated to "CQ") is particularly preferable. As the reducing agent, for example, primary amine, secondary amine or tertiary amine is preferable, and dimethylaminoethyl methacrylate of tertiary amine is particularly preferable. A tin compound of dibutyltin dilaurate is also preferable.

The following Examples and Comparative Examples further illustrate the present invention in detail. (Preparation of silane-treated silica-dispersed uniformly in urethane (meth) acrylate)

(1) Silane-treated silica-dispersed uniformly in urethane (meth)acrylate composition I To 600 g of isopropyl alcohol dispersion type colloidal silica (silica content: 30% by weight) having an average particle diameter of 10 to 15 nm and a viscosity of 3 to 20 cps (20° C.), trade name [Snowtex IPA-ST (manufactured by Nissan Chemical Industries, Ltd.), hereinafter abbreviated to "IPA-ST"], 67.2 g of γ-methacryloxypropyltrimethoxysilane and 18.0 g of an 0.01 N hydrochloric acid were added, and the mixture was heated to 70° C. One hour after heating, the reaction solution was filtered and silica deposited on the reaction solution level was removed. Then, the reaction solution was gently stirred with adding 360.0 g of UDMA and the volatile content was distilled off at 40° C. under reduced pressure to obtain a silane-treated silica-dispersed uniformly in urethane (meth)acrylate (hereinafter abbreviated to "SA-1"). The transmittance at 380 to 780 nm of this composition was measured by a photometer. As a result, the composition showed the transmittance of not less than 90%. After polymerizing this composition, the transmittance was measured in the same way. As a result, it was 89.0%. The solid content ($SiO_2$) calculated from the ash content after calcining SA-1 in a crucible was 29.3% by weight.

(2) Silane-treated silica-dispersed uniformly in urethane (meth)acrylate composition 2

To 600 g of IPA-ST, 33.6 g of γ-methacryloxypropyltrimethoxysilane, 33.6 g of phenyltrimethoxysilane and 16.0 g of an aqueous 0.01 N hydrochloric acid solution were added, and the mixture was heated to 70° C. One hour after heating, the reaction solution was filtered and silica deposited on the reaction solution level was removed. Then, the reaction solution was gently stirred with adding 360.0 g of UDMA and the volatile content was distilled off at 40° C. under reduced pressure to obtain a silane-treated silica-dispersed(uniformly) urethane (meth) acrylate (hereinafter abbreviated to "SA-2"). The transmittance at 380 to 780 nm of this composition was measured by a photometer. As a result, the composition showed the transmittance of not less than 90%. After polymerizing this composition, the transmittance was measured in the same way. As a result, it was 89.5%. The solid content ($SiO_2$) calculated from the ash content after calcining SA-2 in a crucible was 29.0% by weight.

[Preparation of a homogeneous composition containing a poly(alkyl methacrylate) and an urethane (meth)acrylate showing neither solubility nor swelling properties to the poly(alkyl methacrylate)]

(1) A homogeneous composition 1:

2-HEMA (260.3 g, 2 mol) was charged in a glass flask equipped with a stirring blade, and then heated to 40 to 50° C. with blowing a nitrogen gas. With stirring at a rate of 50 to 80 rpm, 5.2 g of PMMA was added gradually over 3 to 5 hours and completely swelled and dissolved. To the resulting solution, 110 mg of dibutyltin dilaurate was added. After the completion of the addition, blowing of the nitrogen gas was terminated and the atmosphere in the flask was replaced by oxygen. With passing through an oxygen gas, TMDI (210.3 g, 1 mol) was added dropwise over 2 hours. After the completion of the dropwise addition, the mixture was heated to 70±1° C. and the addition reaction was continued until all isocyanate groups were reacted to obtain a curable composition (hereinafter abbreviated to "B-1"). The reaction end point was confirmed by the isocyanate equivalent titration method. The yield was 98.6%.

The reaction end point according to the isocyanate equivalent titration method was measured by the following method. (1) Weigh accurately 3 g of a sample and transfer to a glass-stoppered conical flask. (2) Add properly 50 ml of di-n-butylamine solution to the sample and allow to stand for 15 minutes. (3) After adding 20 ml of the 1st grade reagent, isopropyl alcohol, add 3 to 4 drops of a bromocresol green indicator (add 1.5 ml of a N/11 sodium hydroxide solution to 0.1 g of bromocresol green, grind sufficiently to dissolve the bromocresol green, and add water to make 100 ml), and mix sufficiently. (4) Then, titrate with N/2 hydrochloric acid. At about the end point, add N/2 hydrochloric acid drop by drop and continue the titration with shaking the solution every time. Take the point, where a blue or bluish violet color disappear and the produced yellow color continues at least 15 seconds, as the end point. In this test, perform a blank test under the same conditions.

$$\text{Isocyanate equivalent} = \frac{(B - A) \times f}{2 \times S}$$

where A: amount (ml) of a N/2 hydrochloric acid standard solution used in a run proper B: amount (ml) of a N/2 hydrochloric acid standard solution used in a blank test f: factor of a N/2 hydrochloric acid standard solution S: amount (g) of a sample collected (2) A homogeneous composition 2:

According to the same manner as that described in B-1 except for changing the amount of PMMA to 9.4 g, a composition (hereinafter abbreviated to "B-2") was obtained (yield 99.5%).

(2) A homogeneous composition 3:

According to the same manner as that described in B-1 except for using 5.2 g of PEMA in place of PMMA, a composition (hereinafter abbreviated to "B-3") was obtained (yield 99%).

(4) A homogeneous composition 4:

According to the same manner as that described in B-3 except for using 9.4 g of PEMA, a composition (hereinafter abbreviated to "B-4") was obtained (yield 98%).

(5) A homogeneous composition 5:

TMDI (210.3 g, 1 mol) was charged in a glass flask equipped with a stirring blade, and then heated to 40 to 50° C. with blowing a nitrogen gas. With stirring at a rate of 50 to 80 rpm, 9.4 g of PEMA was added by several portions over 3 to 5 hours and completely swelled/dissolved.

To the resulting solution, 110 mg of dibutyltin dilaurate was added. After the completion of the addition, blowing of the nitrogen gas was terminated and the atmosphere in the flask was replaced by oxygen. With passing through an oxygen gas, 2-HEMA (260.3 g, 2 mol) was added dropwise over 2 hours. After the completion of the dropwise addition, the mixture was heated to 70±1° C. and the addition reaction was continued until all isocyanate groups were reacted. The reaction end point was confirmed by FT-IR and isocyanate equivalent titration method to obtain a homogeneous composition containing a poly(alkyl methacrylate) and an urethane (meth)acrylate showing neither solubility nor swelling properties to the poly(alkyl methacrylate) (hereinafter abbreviated to "B-5") (yield 98.2%).

(6) A homogeneous composition 6:

According to the same manner as that described in B-5 except for using 47 g of PEMA, a composition (hereinafter abbreviated to "B-6") was obtained (yield 98%).

(7) A homogeneous composition 7:

HMDI (168.20 g, 1 mol) was charged in a glass flask equipped with a stirring blade, and then heated to 40 to 50° C. with blowing a nitrogen gas. With stirring at a rate of 50 to 80 rpm, 10 g of PEMA was added by several portions over 3 to 5 hours and completely swelled/dissolved. To the resulting solution, 110 mg of dibutyltin dilaurate was added. After the completion of the addition, blowing of the nitrogen gas was terminated and the atmosphere in the flask was replaced by oxygen. With passing through an oxygen gas, 2-HFPA (444.5 g, 2 mol) was added dropwise over 2 hours. After the completion of the dropwise addition, the mixture was heated to 50±1° C. and the addition reaction was continued until all isocyanate groups were reacted to obtain 1,6-bis[(2-phenoxy-2'-acryloxy)isopropyl-oxycarbonylamino]hexane (hereinafter abbreviated to "UDA"). The reaction end point was confirmed by FT-IR and isocyanate equivalent titration method to obtain a composition wherein urethane (meth)acrylate showing neither solubility nor swelling properties to poly(alkyl methacrylate) is homogeneously blended (hereinafter abbreviated to "B-7").

(8) A homogeneous composition 8:

HMDI (504.6 g, 3 mol) was charged in a glass flask equipped with a stirring blade, and then heated to 40 to 50° C. with blowing a nitrogen gas. With stirring at a rate of 50 to 80 rpm, 9 g of PEMA was added by several portions over 3 to 5 hours and completely swelled/dissolved.

To the resulting solution, 10 mg of dibutyltin dilaurate was added. After the completion of the addition, blowing of the nitrogen gas was terminated and the atmosphere in the flask was replaced by oxygen. With passing through an oxygen gas, trimethylolpropane (hereinafter abbreviated to "TMP") (134.18 g, 1 mol) was added dropwise over 2 hours. After the completion of the dropwise addition, the mixture was heated to 50±1° C. and the addition reaction between one isocyanate of HMDI and TMP was performed.

After the completion of the addition reaction, 110 mg of dibutyltin dilaurate was added. After the completion of the addition, 2-HFPA (666.75 g, 3 mol) was added dropwise over 2 hours. After the completion of the dropwise addition, the mixture was heated to 70±1° C. and the addition reaction was continued until all isocyanate groups were reacted to obtain trifunctional urethane acrylate oligomer 1,1,1-tri[6-[(1-acryloxy-3-phenoxy) isopropyloxycarbanylamino]-hexylcarbamoyloxymethy]propane (hereinafter abbreviated to "URO"). The reaction end point was confirmed by FT-IR and isocyanate equivalent titration method to obtain a homogeneous composition (hereinafter abbreviated to "B-8") was obtained (yield 98.5%).

The homogeneous compositions B-1 to B-8 were respectively confirmed by measuring each characteristic absorption using FT-IR (FT-300) (manufactured by Horiba, Ltd.) and measuring the average molecular weight and retention time of the polymer as well as those of the urethane monomer using GPC.

EXAMPLES

Example 1

A mixed solution of MMA (5 g) and SA-1 (5 g) was mixed with a polymer PMMA-1 (average molecular weight: 1,000, 000, average particle diameter: B micron PMMA) in a weight ratio of 1:1. As the method of mixing the mixed solution with PMMA-1, there can be used methods such as (1) mortar mixing, (2) vessel mixing, (3) ball mill mixing, etc., but mixing was performed using [a laboratory planetary ball mill P-5], (manufactured by Flitchu Japan Co., Ltd.) in this Example. The mixing ratio of the mixed solution to the polymer is 10 g/10 g. The mixing conditions is as follows: room temperature, 100 rpm, mixing time of 10 minutes and 4 pebbles (10 mm$\phi$).

After the polymer was swollen with the monomer, a rubber elastic material was produced in a mold under a pressure of 20 to 80 Kgf/cm$^2$ for 10 to 25 minutes. A change in rubber hardness with a lapse of time and that in shear modulus with a lapse of time of the resulting rubber elastic material were shown in Table 1 and Table 2, respectively. The rubber elastic material maintained the rubber elasticity state for 2 years without polymerizing.

Example 2

According to the same manner as that described in Example 1 except for using MMA (5 g), SA-1 (4 g) and TMP (1 g) in place of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 3

According to the same manner as that described in Example 1 except for using MMA (5 g), SA-1 (4 g) and TMP (1 g) in place of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 4

According to the same manner as that described in Example 1 except for using a mixed solution of MMA (3 g), SA-1 (5 g), TMP (10 g) and PPZ (1 g) in place of the mixed solution of MMA (5 g) and SA-1 (5 g) and using PEMA (average molecular weight: 450,000, average particle diameter: 20 to 25 $\mu$m) as the polymer, a rubber elastic material was produced and evaluated. The rubber elastic material maintained the rubber elasticity state for 2 years without polymerizing. The results are shown in Table 1 and Table 2.

Example 5

According to the same manner as that described in Example 4 except for using a mixture of PMMA-1 and PEA used in Example 4 in a weight ratio of 1:1 as the polymer, a rubber elastic material was produced and evaluated. The rubber elastic material maintained the rubber elasticity state for 2 years without polymerizing. The results are shown in Table 1 and Table 2.

Example 6

According to the same manner as that described in Example 1 except for using a mixed solution of MMA (5 g), SA-1 (4.5 g) and TMP (0.5 g) in place of the mixed solution of MMA (5 g) and SA-1 (4.5 g), a rubber elastic material was produced and evaluated. The rubber elastic material maintained the rubber elasticity state for 2 years without polymerizing. The results are shown in Table 1 and Table 2.

Example 7

According to the same manner as that described in Example 1 except for using MMA (5 g), SA-1 (4 g) and B-5 (1 g) in place of the mixed solution of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 8

According to the same manner as that described in Example 1 except for using a mixed solution of MMA (5 g), SA-1 (4 g), TMP (5 g) and DMP (0.5 g) in place of the mixed solution of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 9

According to the same manner as that described in Example 1 except for using a mixed solution of MMA (5 g), SA-1 (4 g), PPZ (0.5 g) and DMP (0.5 g) in place of the mixed solution of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 10

According to the same manner as that described in Example 1 except for using a mixed solution of MMA (5 g), SA-2 (3.8 g), B-5 (1 g) and DBP (0.2 g) in place of the mixed solution of MMA (5 g) and SA-1 (5 g), a rubber elastic material was produced and evaluated. The rubber elastic material maintained the rubber elasticity state for 2 years without polymerizing. The results are shown in Table 1 and Table 2.

Example 11–17

According to the same manner as that described in Example 7 except for using compositions B-1, B-2, B-3, B-4, B-6, B-7 and B-8 in place of the composition B-5, a rubber elastic material was produced. The rubber elastic material maintained the rubber elasticity state for 2 years without polymerizing. The results are shown in Table 1 and Table 2.

Comparative Example 1

According to the same manner as that described in Example 1, a rubber elastic material was produced using an cold-polymerizable resin for dental crown "Adfar" (manufactured by Shofu Co., Ltd.). About 9 to 10 minutes after mixing, the rubber elastic material was cured. The rubber hardness was not less than 92 and the shear modulus could not be measured. The results are shown in Table I and Table 2.

TABLE 1

| | days lapsed | | | | | | | | | |
|---|---|---|---|---|---|---|---|---|---|---|
| Example | 1 day | 5 day | 7 day | 21 day | 30 day | 40 day | 6 month | 10 month | 14 month | 25 month |
| 1 | 53 | 73 | 73 | 75 | 77 | 77 | 78 | 80 | 80 | 80 |
| 2 | 49 | 69 | 70 | 72 | 75 | 80 | 80 | 82 | 82 | 82 |
| 3 | 52 | 70 | 74 | 74 | 75 | 84 | 82 | 84 | 82 | 82 |
| 4 | 43 | 52 | 50 | 51 | 54 | 54 | 57 | 56 | 56 | 58 |
| 5 | 28 | 40 | 53 | 53 | 53 | 54 | 54 | 54 | 53 | 53 |
| 6 | 48 | 68 | 68 | 72 | 75 | 78 | 80 | 78 | 82 | 81 |
| 7 | 47 | 47 | 51 | 51 | 55 | 52 | 52 | 53 | 52 | 52 |
| 8 | 47 | 49 | 51 | 52 | 55 | 52 | 52 | 54 | 53 | 53 |
| 9 | 47 | 49 | 49 | 51 | 52 | 52 | 52 | 52 | 52 | 52 |
| 10 | 46 | 49 | 50 | 52 | 54 | 52 | 52 | 53 | 52 | 52 |
| 11 | 54 | 70 | 73 | 76 | 75 | 76 | 77 | 80 | 78 | 78 |
| 12 | 48 | 50 | 53 | 52 | 52 | 54 | 55 | 56 | 58 | 59 |
| 13 | 48 | 50 | 53 | 52 | 53 | 54 | 57 | 56 | 57 | 58 |
| 14 | 47 | 49 | 51 | 51 | 55 | 52 | 52 | 53 | 52 | 53 |
| 15 | 46 | 47 | 50 | 50 | 54 | 52 | 53 | 53 | 53 | 54 |
| 16 | 40 | 42 | 40 | 42 | 43 | 42 | 43 | 42 | 44 | 44 |
| 17 | 45 | 47 | 49 | 49 | 53 | 50 | 50 | 51 | 50 | 50 |
| Comp. Ex. 1 | 94 | 94 | 97 | 97 | 97 | 98 | 97 | 97 | 98 | 98 |

TABLE II

| | days lapsed | | | | | | | | | |
|---|---|---|---|---|---|---|---|---|---|---|
| Example | 1 day | 5 day | 7 day | 21 day | 30 day | 40 day | 6 month | 10 month | 24 month |
| 1 | $1.73 \times 10^6$ | $1.65 \times 10^7$ | $2.52 \times 10^7$ | $3.19 \times 10^7$ | $1.05 \times 10^8$ | $1.25 \times 10^8$ | $1.65 \times 10^8$ | $2.15 \times 10^6$ | $1.98 \times 10^8$ |
| 2 | $1.05 \times 10^6$ | $1.01 \times 10^7$ | $1.51 \times 10^7$ | $2.17 \times 10^7$ | $2.97 \times 10^7$ | $4.25 \times 10^7$ | $6.54 \times 10^7$ | $1.25 \times 10^8$ | $1.45 \times 10^8$ |
| 3 | $1.02 \times 10^5$ | $1.85 \times 10^7$ | $2.57 \times 10^7$ | $5.76 \times 10^7$ | $6.95 \times 10^7$ | $1.24 \times 10^8$ | $1.35 \times 10^8$ | $2.75 \times 10^8$ | $1.98 \times 10^8$ |
| 4 | $4.51 \times 10^5$ | $6.21 \times 10^5$ | $9.40 \times 10^5$ | $1.02 \times 10^6$ | $1.33 \times 10^6$ | $3.25 \times 10^6$ | $4.85 \times 10^6$ | $4.75 \times 10^6$ | $5.25 \times 10^6$ |
| 5 | $4.85 \times 10^5$ | $9.50 \times 10^5$ | $1.53 \times 10^5$ | $1.94 \times 10^6$ | $3.22 \times 10^6$ | $4.25 \times 10^6$ | $4.05 \times 10^6$ | $5.25 \times 10^6$ | $6.25 \times 10^6$ |
| 6 | $1.78 \times 10^6$ | $1.70 \times 10^7$ | $3.02 \times 10^7$ | $3.25 \times 10^6$ | $6.25 \times 10^7$ | $1.24 \times 10^8$ | $1.45 \times 10^8$ | $2.85 \times 10^8$ | $2.04 \times 10^8$ |

TABLE II-continued

| | days lapsed | | | | | | | | |
|---|---|---|---|---|---|---|---|---|---|
| Example | 1 day | 5 day | 7 day | 21 day | 30 day | 40 day | 6 month | 10 month | 24 month |
| 7 | $5.60 \times 10^5$ | $8.25 \times 10^6$ | $6.81 \times 10^6$ | $6.25 \times 10^6$ | $6.24 \times 10^6$ | $4.88 \times 10^6$ | $4.95 \times 10^6$ | $5.06 \times 10^6$ | $5.07 \times 10^6$ |
| 8 | $4.88 \times 10^5$ | $8.61 \times 10^6$ | $8.06 \times 10^6$ | $6.85 \times 10^6$ | $6.62 \times 10^6$ | $4.88 \times 10^6$ | $5.05 \times 10^6$ | $5.85 \times 10^6$ | $6.25 \times 10^6$ |
| 9 | $5.51 \times 10^5$ | $9.01 \times 10^6$ | $6.78 \times 10^6$ | $6.26 \times 10^6$ | $5.98 \times 10^6$ | $5.96 \times 10^6$ | $6.05 \times 10^6$ | $7.90 \times 10^6$ | $9.41 \times 10^6$ |
| 10 | $4.78 \times 10^5$ | $9.74 \times 10^6$ | $7.36 \times 10^6$ | $6.34 \times 10^6$ | $6.15 \times 10^6$ | $4.61 \times 10^6$ | $6.06 \times 10^6$ | $7.91 \times 10^6$ | $8.68 \times 10^6$ |
| 11 | $1.85 \times 10^6$ | $1.75 \times 10^7$ | $2.54 \times 10^7$ | $3.29 \times 10^7$ | $1.24 \times 10^8$ | $1.29 \times 10^8$ | $1.25 \times 10^8$ | $1.95 \times 10^8$ | $2.42 \times 10^8$ |
| 12 | $4.88 \times 10^5$ | $8.62 \times 10^6$ | $8.06 \times 10^6$ | $3.85 \times 10^6$ | $6.95 \times 10^6$ | $7.05 \times 10^6$ | $6.95 \times 10^6$ | $6.55 \times 10^6$ | $6.35 \times 10^6$ |
| 13 | $4.95 \times 10^5$ | $8.59 \times 10^6$ | $8.21 \times 10^6$ | $6.26 \times 10^6$ | $6.85 \times 10^6$ | $6.98 \times 10^6$ | $6.99 \times 10^6$ | $6.45 \times 10^6$ | $6.45 \times 10^6$ |
| 14 | $5.05 \times 10^5$ | $8.70 \times 10^6$ | $8.29 \times 10^6$ | $6.45 \times 10^6$ | $6.90 \times 10^6$ | $6.75 \times 10^6$ | $6.54 \times 10^6$ | $6.25 \times 10^6$ | $6.09 \times 10^6$ |
| 15 | $5.25 \times 10^5$ | $8.72 \times 10^6$ | $8.15 \times 10^6$ | $6.55 \times 10^6$ | $6.75 \times 10^6$ | $7.15 \times 10^6$ | $7.35 \times 10^6$ | $7.05 \times 10^6$ | $6.95 \times 10^6$ |
| 16 | $2.95 \times 10^5$ | $9.15 \times 10^5$ | $3.81 \times 10^6$ | $3.45 \times 10^6$ | $3.75 \times 10^6$ | $3.85 \times 10^6$ | $2.95 \times 10^6$ | $3.05 \times 10^6$ | $3.25 \times 10^6$ |
| 17 | $5.05 \times 10^5$ | $6.25 \times 10^6$ | $5.95 \times 10^6$ | $4.98 \times 10^6$ | $5.25 \times 10^6$ | $5.45 \times 10^6$ | $5.35 \times 10^6$ | $4.98 \times 10^6$ | $4.85 \times 10^6$ |
| Comp. Ex. 1 | | | | determination is impossible | | | | | |

[Evaluation method of rubber elastic material characteristics]

Rubber hardness:

The rubber hardness was measured at 23° C.±1.5° C. using a hardness tester, type C (manufactured by Kobunshi Seiki Co., Ltd.).

Shear modulus:

The shear modulus was measured by using DMS110 (manufactured by Seiko Denshi Kogyo Co., Ltd.). The measurement was performed under the conditions of an area of 66.61 mm$^2$, a temperature of 23° C., a displacement of 100 μm and a frequency of 0.01 Hz, using a sample (thickness: 1.45±0.02 mm, length: 7.17±0.02 mm, width: 9.29±0.02 mm). The shear modulus due to DMS110 was determined according to the following equation.

[Numerical 2]

$$K = \frac{EG}{9G - 3E} \quad (1)$$

$$\sigma = \frac{E - 2G}{2G} \quad (2)$$

With respect to a lot of materials which can be an object the measurement of a viscoelasticity, σ-0.5 is established. Using the equation (2), we have the equation: E=3G.

E: Young's modulus (elongation modulus and longitudinal modulus)
G: Shear modulus
K: Volume modulus
σ: Poisson ratio Examples 18 to 27

Using the same compositions as those of Examples 1 to 10 except for adding 0.06 g of BPO to 10 g of the mixed solutions of Examples 1 to 10, a biorestorative material was produced under the following conditions, respectively.

After the polymer is sufficiently swollen with the monomer, a biorestorative material was produced in a mold under a pressure of 20 to 80 Kgf/cm$^2$ for 10 to 20 minutes and removing from the mold. Under atmospheric pressure, the biorestorative material was polymerized at 80° C. for 5 minutes, polymerized at 120° C. for 10 minutes, and then annealed at 100° C. for 8 hrs. The hardness, bending characteristics (e.g. strength, energy, modulus, etc.) and transmittance of the resulting polymer were measured. The biorestorative materials were polymerized by storage at 5° C. for 1 day and 14 months, respectively, under the above conditions and they were taken as a sample for evaluation of physical properties. In all Examples 18 to 37, deterioration of physical properties did not arise. The results are shown in Table 3.

Comparative Example 2

Using an cold-polymerizable resin for dental crown "Adfar" (manufactured by Shofu Co., Ltd.), the same operation as that described in Examples 18 to 27 was performed. The results are shown in Table 3.

Examples 28 to 37

Using the same compositions as those of Examples 1 to 10 except for adding 0.02 g of CQ and 0.042 g of dibutyltin dilaurate to 10 g of the mixed solutions of Examples 1 to 10, a biorestorative material was produced, respectively. In Examples 28 to 37, deterioration of physical properties did not arise. The results are shown in Table 3.

The polymerization of the biorestorative material was performed by using a photopolymerizer [photopolymerizer Twin, manufactured by Shofu Co., Ltd.]. The irradiation time was from 3 to 5 minutes.

TABLE 3

| | composition | | bending properties | | | |
|---|---|---|---|---|---|---|
| Example | represented by Ex. No. | hardness | strength (MPa) | energy (g-cm) | transmittance (%) | abrasion amount (%) |
| 18 | Ex. 1 | 17.5(17.9) | 100.55(108.25) | 225.45(228.54) | 68.9(67.5) | 2.08(2.15) |
| 19 | Ex. 2 | 21.1(21.5) | 97.42(105.15) | 237.76(245.25) | 69.8(70.5) | 1.80(1.85) |
| 20 | Ex. 3 | 21.0(21.6) | 101.74(105.65) | 253.12(256.25) | 71.6(70.7) | 1.55(1.50) |
| 21 | Ex. 4 | 16.5(16.5) | 85.45(90.24) | 247.25(250.45) | 68.5(68.5) | 2.85(2.40) |

TABLE 3-continued

| Example | composition represented by Ex. No. | hardness | bending properties strength (MPa) | bending properties energy (g-cm) | transmittance (%) | abrasion amount (%) |
|---|---|---|---|---|---|---|
| 22 | Ex. 5 | 17.5(17.8) | 92.56(94.52) | 225.25(215.45) | 67.5(67.5) | 2.65(2.75) |
| 23 | Ex. 6 | 20.9(21.0) | 105.45(105.24) | 237.45(240.52) | 70.5(70.6) | 1.81(1.65) |
| 24 | Ex. 7 | 16.9(17.5) | 100.50(102.50) | 241.07(252.09) | 65.5(65.5) | 2.25(2.28) |
| 25 | Ex. 8 | 17.8(18.0) | 94.66(97.75) | 221.35(225.45) | 62.5(64.0) | 2.45(2.56) |
| 26 | Ex. 9 | 17.6(18.0) | 102.55(108.95) | 260.26(270.25) | 67.5(68.0) | 2.35(2.75) |
| 27 | Ex. 10 | 18.0(18.2) | 103.95(105.25) | 265.25(270.58) | 67.9(65.5) | 2.35(2.75) |
| 28 | Ex. 1 | 14.5(1.57) | 91.35(92.54) | 222.14(212.55) | 59.8(60.5) | 2.59(2.45) |
| 29 | Ex. 2 | 15.5(15.8) | 90.54(90.98) | 211.24(215.69) | 60.5(61.5) | 2.45(2.48) |
| 30 | Ex. 3 | 17.5(17.8) | 95.78(96.89) | 215.69(210.36) | 68.5(65.8) | 2.08(1.69) |
| 31 | Ex. 4 | 14.0(14.2) | 80.56(82.56) | 200.36(198.26) | 62.5(63.6) | 3.05(2.98) |
| 32 | Ex. 5 | 15.6(15.6) | 85.69(84.23) | 185.26(196.36) | 62.5(63.6) | 2.78(2.69) |
| 33 | Ex. 5 | 18.9(18.2) | 95.69(92.69) | 205.36(212.36) | 68.5(65.9) | 1.96(2.10) |
| 34 | Ex. 7 | 14.3(14.2) | 90.26(92.36) | 215.36(224.36) | 60.3(61.3) | 2.39(2.56) |
| 35 | Ex. 8 | 16.2(14.5) | 85.69(82.36) | 200.36(198.56) | 59.6(58.6) | 2.89(2.78) |
| 36 | Ex. 9 | 15.6(14.9) | 96.98(92.36) | 236.36(229.69) | 62.5(63.6) | 2.98(2.87) |
| 37 | Ex. 10 | 16.5(15.9) | 98.69(95.35) | 236.45(222.12) | 65.3(64.3) | 2.87(2.68) |
| Comp. Ex. 2 | | 14.60 | 85.81 | 185.56 | 68.9 | 4.58 |

The value in ( ) shows the date of test materials polymerized after hold at 5° C. for 14 month.

[Evaluation of physical properties of biorestorative material]

Measurement of hardness:

The Knoop hardness after storage in water at 50° C. for 24 hours was measured by using a hardness tester DMH-2 (manufactured by Matsuzawa Seiki Co., Ltd.). The load was 25 g.

Measurement of bending strength:

A sample (2 mm in width×2 mm in thickness×25 mm in length) was made, using a autograph AG5000B (manufactured by Simazu Corp.), and the strength (maximum bending strength) and energy (shattering energy) after storage in water at 50° C. for 24 hours were measured. The number of sample was 5. The measuring conditions were as follows: a distance between the supports: 20 mm, cross-head speed: 1 mm/min.

Transmittance:

It was measured at the wavelength within the range from 780 to 380 nm, using a spectrophotometer U-3200 (manufactured by Hitachi Corp.).

Abrasion amount:

The abrasion amount after the tooth brush abrasion test was measured. The measuring conditions were as follows: kind of tooth brush: Between (manufactured by Sunstar Co., Ltd.), size of sample: 15 mm in length×20 mm in width×2.5 mm in thickness, number of samples: 4, load: 185 g, dentifrice: toothpaste Green Sunstar, number of brushing: 30,000.

[Production of artificial tooth]

Examples 38 to 47

According to the same manner as that described in Examples 1 to 10 except for adding 0.06 g of BPO to 10 g of each mixed solution, and 0.01 g of a pigment to 10.0 g of PMAA-1 in Examples 1 to 10, an enamel color of the artificial tooth was produced. According to the same manner as that described above except for changing only the amount of the pigment, an dentinal color and a base color of each mixed solution were produced.

After MMA was swollen, an artificial tooth was produced by using a C5 central incisor mold of a rigid resin tooth "Endula Anterio" (manufactured by Shofu Co., Ltd.). Regarding the first molding, a raw material for enamel color was pressed under the pressure of 40 to 100 Kgf/cm$^2$ for 10 to 15 minutes, and then a raw material for dentinal color was pressed under the pressure of 40 to 100 Kgf/cm$^2$ for 10 to 15 minutes. Finally, a raw material for base color was pressed under the pressure of 40 to 100 Kgf/cm$^2$ and a biorestorative material having the form of the artificial tooth was removed from the mold. Despite the multi-layer molding, little burr arose. If necessary, burr at the excessive portion can be removed by using scissors or a sharp cutting knife. After the completion of the polymerization, the artificial tooth had little flash and correction of burr was not required. The thickness of burr after the completion of the molding is shown in Table 4.

The artificial tooth was polymerized at 80° C. for 10 minutes, cooled and then polymerized at 120° C. for 10 minutes. Alternatively, the artificial tooth may be polymerized at 80° C., followed by polymerization at 120° C. for 10 minutes. After the completion of the polymerization, the artificial tooth was annealed at 100° C. for 8 hours.

Comparative Example 3

After coloring PMMA as a normal acrylic artificial tooth material, i.e. enamel color, dentinal color and base color, a mixture of PMMA and MMA was heated under pressure using the same mold as that used in Examples 39 to 48, followed by stepwise molding with changing the molds of the enamel portion, dentinal portion and base portion in order to obtain an artificial tooth. In all artificial tooth, burr requiring correction arose. The thickness of burr after molding is shown in Table 4.

The enamel portion, dentinal portion and base portion were molded under a preliminary pressure of 200 to 300 Kgf/cm$^2$ for 2 to 5 minutes, and then 1000–3000 kgf/cm$^2$ at an optional temperature within the range from 60 to 130° C. for 10 minutes. After the completion of each portion, cooling was conducted for 5 minutes. After the completion of the polymerization, the artificial tooth was removed from the mold and then annealed at 100° C. for 8 hours.

Comparative Example 4

As the composite raw material used in the enamel portion, 30 g of "Polylite 8000" (manufactured by Dainippon Ink Industries Co., Ltd.), 68.5 g of a borosilicate glass powder (average particle diameter: 20 μm), 0.1 g of water-containing silicic acid "Carplex" (manufactured by Shionogi Seiyaku Co., Ltd.) and 0.5 g of BPO and a pigment as described in the Example 1 in Japanese Patent Application No. 29294/1973 were kneaded by using a "portable kneader PBV-03" (manufactured by Irie Shokai Co., Ltd.) to prepare a composite material. As the raw material of the dentinal portion and base color, the composition of Comparative Example 3 was used and an artificial tooth was produced according to the same manner as that described in Comparative Example 3. All artificial teeth required burr correction. The thickness of flash after completion of the molding is shown in Table 4.

Examples 48 to 50

0.02 g of CQ and 0.042 g of dibutyltin dilaurate were added to 10 g of each mixed solution of Examples 1, 2 and 3 and 0.01 g of a pigment was added to 10 g of PMMA-1, and they were mixed according to the same manner as that described in Examples 1 to 10 to produce an enamel color raw material of the artificial tooth. According to the same manner as that described above except for changing the amount of the pigment, an dentinal color raw material and a base color raw material were produced.

After MMA was swollen, a biorestorative material was produced in a room wherein visible light is screened according to the same manner as that described in Examples 38 to 47.

The polymerization was conducted by using a photopolymerizer [Twin polymerizer, manufactured by Shofu Co., Ltd.]. The molding was conducted at 40° C. for 10 to 15 minutes. After the completion of the polymerization, burr of the artificial tooth did not arose and barelling is not required and the aesthetic property was excellent. The thickness of burr after the completion of the molding is shown in Table 4.

TABLE 4

| Example | composition (Ex. No.) | flash thickness (mm) |
| --- | --- | --- |
| 38 | Ex. 1 | 0.01> |
| 39 | Ex. 2 | 0.01> |
| 40 | Ex. 3 | 0.01> |
| 41 | Ex. 4 | 0.01> |
| 42 | Ex. 5 | 0.01> |
| 43 | Ex. 6 | 0.01> |
| 44 | Ex. 7 | 0.01> |
| 45 | Ex. 8 | 0.01> |
| 46 | Ex. 9 | 0.01> |
| 47 | Ex. 10 | 0.01> |
| 48 | Ex. 1 | 0.01> |
| 49 | Ex. 2 | 0.01> |
| 50 | Ex. 3 | 0.01> |
| comp. Ex. 3 | comp. Ex. 1 | 0.12~0.25 |
| comp. Ex. 4 | composite | 0.15~0.27 |

[Moldability of artificial tooth and evaluation of artificial tooth]

Examples 51 to 63

Using the artificial teeth of Examples 38 to 50, the first stage polymerization was conducted at 65 to 125° C. for 2.5 to 10 minutes and the final stage polymerization was conducted at 105 to 130° C. for 3 to 15 minutes as the molding conditions to produce a lot of artificial teeth under these conditions. With respect to the resulting artificial teeth, crack and turbidity of the enamel portion as well as bonding properties between the enamel portion and dentinal portion and those between the dentinal portion and base portion were studied. This artificial tooth was bonded with a base resin for heat polymerization "Urban" (manufactured by Shofu Co., Ltd.) and the strength of bonding between the base resin and artificial tooth was determined and the repeating impact strength test of the artificial tooth was conducted. All Examples 51 to 63 showed excellent bonding strength and impact strength as the artificial tooth. The molding conditions of the artificial tooth were wide and molding failures did not arose under any conditions. The strength of bonding between the artificial tooth and base resin is shown in Table 5. The molding test results are shown in Table 6.

TABLE 5

| Example | composition (Ex. No.) | bonding strength (Kgf) | impact strength (points) |
| --- | --- | --- | --- |
| 51 | 39 | 24.5 | 26.5 |
| 52 | 40 | 24.9 | 27.5 |
| 53 | 41 | 25.6 | 28.5 |
| 54 | 42 | 23.6 | 26.5 |
| 55 | 43 | 24.0 | 25.5 |
| 56 | 44 | 23.6 | 26.4 |
| 57 | 45 | 24.2 | 26.4 |
| 58 | 46 | 23.9 | 25.9 |
| 59 | 47 | 22.9 | 26.5 |
| 60 | 48 | 23.6 | 24.5 |
| 61 | 49 | 22.5 | 24.3 |
| 62 | 50 | 22.9 | 23.9 |
| 63 | 51 | 23.1 | 24.9 |
| JIS value | | ≧11.0 | |
| real tooth of Shofu | | 15.1 | 21.3 |

TABLE 6

| Example | composition (Ex. No.) | molding condition | the number of tooth in which crack and/or turbidity obserbed | the number of tooth poor in bonding |
| --- | --- | --- | --- | --- |
| 51~63 | Ex. 38~50 | polymerization in 1st stage (65~125° C. optionally 2.5~10 min.) final polymerization (105~130° C. optionally 3~15 min.) | 0/1120 | 0/1120 |

Boning test:

The strength of bonding between the artificial tooth and resin material for dental base was measured by the method defined in 7.5 (bonding test) of JIS T6506 (resin tooth). The results are shown in Table 7.

TABLAE 7

| comp. Ex. | composition (comp. Ex. No.) | molsing time of enamel (° C.-min.) | molding time of dentin (° C.-min.) | molding time of base (° C.-min.) | the number of tooth in which crack and/or turbidity is obserbed | the number of tooth poor in bonding |
|---|---|---|---|---|---|---|
| 5 | 3 | 70-5 | 70-5 | 125-5 | 0/28 | 0/28 |
|   |   | 75-5 | 75-5 | 125-5 | 0/28 | 0/28 |
|   |   | 80-5 | 80-5 | 125-5 | 0/28 | 1/28 |
|   |   | 85-5 | 85-5 | 125-5 | 2/28 | 2/28 |
|   |   | 90-5 | 90-5 | 125-5 | 0/28 | 4/28 |
|   |   | 95-5 | 95-5 | 125-5 | 1/28 | 4/28 |
|   |   | 100-5 | 100-5 | 125-5 | 2/28 | 8/28 |
| 6 | 4 | 70-5 | 70-5 | 127-5 | 14/28 | 0/28 |
|   |   | 75-5 | 75-5 | 127-5 | 10/28 | 0/28 |
|   |   | 80-5 | 80-5 | 127-5 | 3/28 | 0/28 |
|   |   | 85-5 | 85-5 | 127-5 | 2/28 | 0/28 |
|   |   | 90-5 | 90-5 | 127-5 | 4/28 | 6/28 |
|   |   | 95-5 | 95-5 | 127-5 | 7/28 | 14/28 |

The cutting enamel portion of the lingual surface side of the artificial tooth produced by the method defined in 7.5 (bonding test) of JIS T6506 (resin tooth) was cut vertically to the main axis, and a stainless steel bar having a diameter of 1 mm was repeatedly dropped on the center portion from the position with the height of 10 mm. Then, the impact strength of the artificial tooth was evaluated by the number of dropping and dropping load. The method of calculating scores is shown below.

The first load and number of loading (100 g×1000 times)

The second load and number of loading (150 g×1000 times)

The third load and number of loading (200 g×1000 times)

Regarding the calculation of the impact strength, the total of numerical values obtained by dividing the number of impact at each stage by 100 was taken as a score. For example, the maximum impact strength becomes (1000/100+1000/100+1000/100=30) if the artificial tooth is not broken after repeating impact of each 1000 times under the load of 100, 150 and 200 g.

Bonding test:

The bonding property between the enamel portion and dentinal portion was confirmed by the above repeating impact test. At the same time, the repeating strength test of the artificial tooth was also conducted. The measurement was conducted after storage in water at 50° C. for 7 days.

Comparative Examples 5 and 6

Using the mixture obtained in Comparative Examples 3 and 4, an artificial tooth was molded under the molding conditions described in Table 7, respectively. The resulting artificial tooth was evaluated according to the same manner as that described in Examples 51 to 63. Regarding the molded article, bonding failures as severe failures of the artificial tooth arose between the enamel portion and dentinal portion and between the dentinal portion and base portion. Regarding the moldability, the suitable conditions range is narrow and the crack and turbidity arose. The results are shown in Table 7.

[Evaluation of dental crown restorative material]

Examples 64 to 66

The enamel color mixtures obtained in Examples 48, 49 and 50 were pressed in an anterior tooth mold (T5 central incisor canine) of a rigid resin tooth "Endura Anterio" (manufactured by Shofu Co., Ltd.) under 20 to 80 Kgf/cm$^2$ for 5 to 10 minutes, respectively. After the completion of the pressing, the enamel material removed from the mold was intraorally mounted and bonded using a dental bonding agent after morphological correction. After the completion of the bonding, visible light was irradiated for 120 seconds to polymerize the enamel material, thereby repairing the dental crown. The restored piece is superior in aesthetic property and bonding properties and, therefore, it could be handled very easily. As the dental bonding agent, both photopolymerizable and cold-polymerizableizable bonding agents can be used. When intraoral restoration is directly conducted, non-irritant one is preferable in case of the cold-polymerization. In order to impart better aesthetic property, a rigid resin veneer material "Solidex" (manufactured by Shofu Co., Ltd.) may be used at the back of the enamel material.

Examples 67 to 69

The enamel color raw materials obtained in Examples 48, 49 and 50 were pressed in a molar tooth mold (M30 lower second dens molaris) of a rigid resin tooth "Endura Posterio" (manufactured by Shofu Co., Ltd.) under 20 to 80 Kgf/cm$^2$ for 10 to 15 minutes to produce an enamel portion material, respectively. After the enamel portion material was removed from the mold and occlusal adjustment was previously performed on an impression model, it was intraorally mounted. The occlusion was reconfirmed, and then the enamel portion material was bonded to an abutment using a dental bonding agent. After the completion of the bonding, visible light was irradiated for 120 seconds to polymerize the enamel portion material, thereby repairing the dental crown. The restored piece is superior in aesthetic property and bonding properties and, therefore, it could be handled very easily. As the dental bonding agent, both photopolymerizable and cold-polymerizable bonding agents can be used. When intraoral restoration is directly conducted, non-irritant one is preferable in case of the cold-polymerization.

[Evaluation as artificial tooth]

Examples 70 to 72

The enamel color raw material, dentinal color raw material and base color raw material obtained in Examples 48, 49 and 50 were pressed in a molar tooth mold (M30 lower second dens molaris) of a rigid resin tooth "Endura Posterio" (manufactured by Shofu Co., Ltd.) under 20 to 80 Kgf/cm$^2$ for 10 to 15 minutes to produce an artificial tooth, respectively. A trial artificial tooth was temporarily mounted to a denture base with missing of M30 lower second dens molaris and occlusal adjustment was intraorally conducted. Then, the trial artificial tooth was bonded to the missing portion using a dental cold-polymerizable resin, followed by photopolymerization. The repaired denture is superior in aesthetic property and adaptability, and the operation was simple and completed in a short period of time.

[Evaluation as movable connector artificial tooth]

Example 73

The enamel color raw material obtained in Example 50 was pressed in a trial connector molar mold (first and second bicuspid of right and left mandibular and maxillary patterns, connector tooth of first and second dens molaris) of a rigid resin tooth "Endura Posterior" (manufactured by Shofu Co., Ltd.) under 20 to 80 Kgf/cm$^2$ for 10 to 15 minutes to produce a movable connector tooth. Using a commercially available material for photopolymerizing base "Tryadresin Material" (manufactured by Dentsply Co., Ltd.), mandibular and maxillary patterns were produced on a plaster cast by a normal method and temporarily polymerized, and then a trial movable connector molar was temporarily arranged. After the completion of the provisional arrangement, rough morphological correction and adjustment of an dental arch were conducted on the cast. Then, it was intraorally mounted and adjustment of the artificial tooth was conducted. After the completion of the adjustment, the artificial tooth was temporarily polymerized again, intraorally. After confirming that the artificial tooth is not deformed, it was removed extraorally and then polymerized on a full-scale. The resulting denture was superior in aesthetic property, strength and adaptability, and had sufficient characteristics as a temporary denture. The operation was simple and completed in a short period of time.

Example 74

The enamel color raw material obtained in Example 50 was pressed in a trial connector molar mold (first and second bicuspid of right and left mandibular and maxillary patterns, connector tooth of first and second dens molaris) of a rigid resin tooth "Endura Posterio" (manufactured by Shofu Co., Ltd.) and a trial connector anterior tooth mold (connector tooth of center canine of C5 right and left mandibular and maxillary patterns) of a rigid resin tooth "Endura Posterio" (manufactured by Shofu Co., Ltd.) under 20 to 80 Kgf/cm$^2$ for 10 to 15 minutes to produce a movable connector tooth. The resulting movable connector tooth was mounted to a wax model denture produced by a normal method. After the arrangement and occlusion were adjusted, polymerization was conducted to produce a denture base. Regarding the denture base, artificial teeth can be easily arranged and were simple and produced in a short period of time.

What is claimed is:

1. A biorestorative material which is a rubbery elastic material and has a shear modulus of $1.0 \times 10^4$ Pa to $9.99 \times 10^9$ Pa at 23° C. and a rubber hardness of 1 to 92. with a Knoop hardness of 10 or more after polymerization, comprising 14.5 to 62.5% by weight of a polymer, 10.0 to 37.5% by weight of a polymerizable monomer, 10.0 to 60.0% by weight of a silane-treated silica-dispersed uniformly iii urethane (meth)acrylate and a polymerization initiator.

2. The biorestorative material according to claim 1, comprising a polymer having an weight average molecular weight of 100,000 to 1,000,000 and an average particle diameter of 1 to 75 μm.

3. A biorestorative material according to claim 1, additionally comprising 0.01 to 25.0 parts by weight of a homogeneous composition containing a poly(alkyl methacrylate) and urethane (meth)acrylate showing neither solubility nor swelling properties to said poly(alkyl methacrylate), and/or 0.01 to 20.0 parts by weight of a plasticizer based on the biorestorative material of claim 2.

4. The biorestorative material according to claim 1, wherein the silane-treated silica-dispersed uniformly in urethane (meth)acrylate is obtained by uniformly dispersing a silane-treated silica which is obtained by treating the surface of colloidal silica whose primary particles have an average particle diameter of 1 to 85 nm with a specific silane compound, in urethane (meth)acrylate.

5. The biorestorative material according to claim 1, wherein the urethane(meth)acrylate has at least one acryloyl group and/or methacryloyl group as well as at least one urethane group in one molecule.

6. The biorestorative material according to claim 3, comprising a phthalic acid ester as the plasticizer.

7. The biorestorative material according to claim 3, comprising a polymer having an weight average molecular weight of 100,000 to 1,000,000 and an average particle diameter of 1 to 75 μm.

8. The biorestorative material according to claim 3, wherein the silane-treated silica-dispersed uniformly in urethane (meth)acrylate is obtained by uniformly dispersing a silane-treated silica which is obtained by treating the surface of colloidal silica whose primary particles have an average particle diameter of 1 to 85 nm with a specific silane compound, in urethane (meth)acrylate.

9. The biorestorative material according to claim 2, wherein the silane-treated silica-dispersed uniformly in urethane (meth)acrylate is obtained by uniformly dispersing a silane-treated silica which is obtained by treating the surface of colloidal silica whose primary particles have an average particle diameter of 1 to 85 mn with a specific silane compound, in urethane (meth)acrylate.

10. The biorestorative material according to claim 3, wherein the urethane(meth)acrylate has at least one acryloyl group and/or methacryloyl group as well as at least one urethane group in one molecule.

11. The biorestorative material according to claim 2, wherein the urethane(meth)acrylate has at least one acryloyl group and/or methacryloyl group as well as at least one urethane group in one molecule.

12. The biorestorative material according to claim 4, wherein the urethane(meth)acrylate has at least one acryloyl group and/or methacryloyl group as well as at least one urethane group in one molecule.

13. The biorestorative material according to claim 2, comprising a phthalic acid ester as the plasticizer.

14. The biorestorative material according to claim 4, comprising a phthalic acid ester as the plasticizer.

15. The biorestorative material according to claim 5. comprising a phthalic acid ester as the plasticizer.

16. A curable dental prosthetic material comprising at least one of biorestorative materials of claim 1.

17. A curable dental prosthetic material comprising at least one of biorestorative materials of claim 3.

18. A curable dental prosthetic material comprising at least one of biorestorative materials of claim 2.

19. A curable dental prosthetic material comprising at least one of biorestorative materials of claim 4.

20. A curable dental prosthetic material comprising at least one of biorestorative materials of claim 5.

21. A curable dental prosthetic material comprising at least one of biorestorative materials of claim 6.

* * * * *